United States Patent [19]

De Backer

[11] Patent Number: 4,650,474
[45] Date of Patent: Mar. 17, 1987

[54] DEVICE FOR ELIMINATION OF URINE THROUGH URETEROSTOMA

[75] Inventor: Emile De Backer, Brussels, Belgium

[73] Assignee: Laboratoires Biotrol, Paris, France

[21] Appl. No.: 684,340

[22] Filed: Dec. 20, 1984

[30] Foreign Application Priority Data

Dec. 20, 1983 [FR] France ............... 83 20386

[51] Int. Cl.⁴ ............................................. A61M 25/02
[52] U.S. Cl. .......................... 604/180; 128/DIG. 26; 604/43; 604/278; 604/328; 604/334
[58] Field of Search ............. 604/27, 43, 54, 94, 604/104, 117, 174–180, 264, 275–279, 280–284, 327, 328, 332, 334; 128/343, DIG. 26

[56] References Cited

U.S. PATENT DOCUMENTS

| 2,617,417 | 11/1952 | Condit | 604/278 |
| 2,759,477 | 8/1956 | Mains | 128/295 |
| 2,865,373 | 12/1958 | Recker | 604/278 |
| 2,898,917 | 8/1959 | Wallace | 128/350 |
| 2,900,979 | 8/1959 | Bishop | 128/283 |
| 2,936,757 | 5/1960 | Trace | 128/276 |
| 3,547,119 | 12/1970 | Hall et al. | 604/180 X |
| 3,572,340 | 3/1971 | Lloyd | 128/278 |
| 3,783,876 | 1/1974 | Dye | 604/117 X |
| 3,884,235 | 5/1975 | Sami | 128/295 |
| 3,927,672 | 12/1975 | Garcia | 128/245 |
| 4,106,507 | 8/1978 | Kellermeyer | 128/295 |
| 4,137,918 | 2/1979 | Bogert | 604/328 |
| 4,265,243 | 5/1981 | Taylor | 128/275 |
| 4,381,765 | 5/1983 | Burton | 604/277 X |
| 4,534,760 | 8/1985 | Raible | 604/328 X |

FOREIGN PATENT DOCUMENTS

| 2329295 | 5/1977 | France . |
| 2511240 | 2/1983 | France . |
| 2105197 | 3/1983 | United Kingdom . |
| 2143740 | 2/1985 | United Kingdom . |
| 2143741 | 2/1985 | United Kingdom . |

Primary Examiner—Dalton L. Truluck
Attorney, Agent, or Firm—Berman, Aisenberg & Platt

[57] ABSTRACT

A device which permits the discharge of urine from cutanenous ureterostomies into the conventional collecting bags, comprising a hollow tube which can optionally divide over a part of its length into two substantially parallel branches a few mm apart, and a flange integral with the tube and adhesive on the face which is directed towards the patient body.

12 Claims, 3 Drawing Figures

DEVICE FOR ELIMINATION OF URINE THROUGH URETEROSTOMA

FIELD OF THE INVENTION

The present invention relates to a device which enables elimination of urine through cutaneous ureterostomas into collecting bags customarily used by individuals who have undergone connection of one or both ureters to the abdominal wall during a surgical operation.

BACKGROUND OF THE ART

Two surgical techniques are currently in use for ureterostomies.

The first technique, known as the Bricker technique, creates an artificial connection between the ureter or ureters to be treated and a fragment of ileum; the isolated fragment of ileum is connected to the skin for discharging the urine going through it, as a consequence of the anastomosis of the ureter or ureters to this fragment. The second technique involves the direct connection of one or both ureters to the skin. Each of these techniques has disadvantages. The first technique is more complicated; furthermore, it can cause ionic imbalance due to reabsorption of various ions through the ileum. Where there is a significant loss of potassium, the organic disorders can cause damages to a greater or lesser extent.

The second technique of cutaneous ureterostomy is surgically simpler, but there is a significant risk of stenosis of the part of the ureter connected to the skin; it has thus been recommended to insert a catheter into this stoma, which catheter must be held in place by some means. These insertions are relatively precarious and the source of many problems.

Furthermore, the urine is discharged into collecting bags which either are fixed directly on the skin around the stoma by means of an adhesive compound placed on the outer face of the bag, or are attached by way of a plate bearing a gum which adheres to the skin, to which plate the collecting bag will be attached by sticking or by a locking system. These devices have numerous disadvantages when used: irritation of the skin due to periodical withdrawal of the bags for hygienic reasons, stoma dimensions non adapted to collecting bag opening diameter, and, above all, problems due to attack by the urine which, when it comes into contact with the adhesive material, unsticks it or results in the loss of adhesive gum properties or even dissolves it.

The device according to the invention, which can be used in the case of cutaneous ureterostomies, eliminates the abovementioned disadvantages and enables the second surgical technique to be used, which is simpler and less detrimental to the patient than the first. For cutaneous ureterostomies, it has also been recommended, for discharging the urine, to implant surgically a device, such as that described in patent FR-A-2,511,240, which is composed of a tube with anchoring points. Such a device, which is irremovable without a further surgical operation, will suffer obvious disadvantages from prolonged use, even when made from fully biocompatible materials; moreover, in the case where a second ureterostomy has to be performed after the first, the latter will have to be reoperated to implant the two-branched device described in the patent application.

Moreover, a device, such as that described in U.S. Pat. No. 3,884,235 for ileostomies and colostomies, is not applicable in the case of ureterostomies. Whereas the system comprising a collecting bag equipped with a connector is sufficiently watertight for collector material of low fluidity issuing from the ileum, this is not the case for the collection of urine; sealing is, in fact, only provided through the contact between the connector and the inside of the ileal passage.

BRIEF DESCRIPTION OF THE DRAWINGS

The three figures are those of schematic perspective views of different embodiments of the invention.

DETAILED DESCRIPTION

Figure 1:
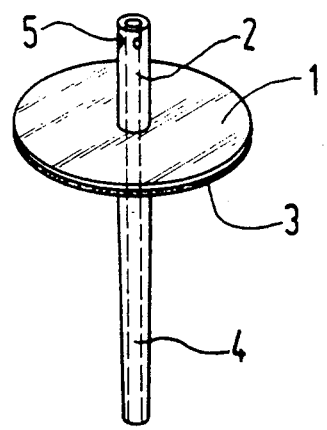

The device according to the invention comprises:

a hollow tube of outer diameter such that the tube can be introduced into the distal end of a ureter after its surgical connection to the abdominal wall, from about 5 cm to 10 cm long and, optionally, of slightly conical shape so that the narrowest part can be easily introduced into the ureter;

a flange or plate integral with this tube, of any shape, but advantageously disk-shaped, which bears, on the face which will be located towards the patient's body, a coating which adheres to the skin and is situated in such a manner that the length of the tube located between the end which is introduced into the stoma and the plate is between approximately 30 mm and 60 mm. The adhesive face of the plate is advantageously protected, until used by a film, such as a sheet of paper, which can be easily removed.

The adhesive flange is preferably of a size such that it can completely cover the inflow opening of the conventional collecting bag, but it can also, optionally, further cover the adhesive zone when the collecting bag incorporates one as a means for attachment to the patient's body.

However, in another embodiment of the invention, the device is connected to a bag for collecting urine by means of a flexible pipe drawn over the outer tube, and the flange can then be smaller. In this case also, the outer tube can be provided with any means for limiting inopportune movement of the pipe on the tube.

The hollow tube can be divided on one side of the plate or flange into two substantially parallel branches a few mm apart, and this then forms a device suitable for patients on whom a double ureterostomy has been performed, and whose stomas have been situated at two sites on the intestinal wall close enough together for each branch to be located in one of the two ureters. In one particular embodiment, the tube is provided, towards the end which is not introduced into the stoma, with lateral perforations through which the urine will drain in the case where one face of the collecting bag adheres to one end of the catheter.

In another embodiments of the invention, this same end of the tube is closed, and the urine will only drain through the lateral perforations, the number and diameter of which will be such that no pressure gradient can arise inside the tube.

These devices can be made of variety of materials, and the same material will preferably be chosen for the tube and the flange, but it is possible to envisage manufacturing these two parts separately and then fixing them together by any known means, particularly by welding. The materials are of necessity biocompatible, nontoxic and not attacked by urine; they can be rigid or flexible; products which are flexible, without being soft, are preferred, so that the device is not the source of trauma, in particular when it is introduced into the ureters, or as a consequence of an impact while the patient is carrying it.

For example polyolefins such as polyethylene or polypropylene, polyamides, polyvinyl chlorides or polytetrafluoroethylenes will be used, and the devide may be manufactured by molding, including injection molding, rotational molding, dip molding or other techniques, according to methods well known to those skilled in the art.

The adhesive substance present on one of the faces of the plate enables the device to be fixed to the patient's body by sticking it to the skin around the stoma; this makes the device completely independent of the collecting bag without in any way possessing the disadvantages of the catheters currently used. This adhesive substance can be distributed over the entire face of the flange, but can also be present at points or in zones. The practitioner will be able to choose a product which is well known in this field, such as an adhesive material based on acrylates or on zinc oxide, which will be applied in a continuous or discontinuous film, a few microns thick, by coating, bonding, welding or other techniques, on the appropriate face of the flange, or such as a non allergenic, stable adhesive synthetic gum, such as that described in patent FR-A-2,479,002, which will be applied in a thin layer from about 0.5 to 2 mm thick, and preferably from about 1 to 1.5 mm thick.

The devices according to the invention have a total length of from about 40 to 80 mm; the hollow tube has an external diameter suited to the diameter of the ureters, that is to say from about 2 to 4 mm for an adult of normal stature; It can be smaller to suit children, or larger when the ureters are dilated for any reason. The internal passage has a diameter of from about 1 to 3 mm, such that the wall of the tube is from about 0.5 to 1 mm thick. The flange is located on the tube at a distance of from about 5 to 15 mm from the end which is not introduced through the stoma. The thickness of the flange or plate is preferably less than 1 mm, and it is made of a material which provides the adhesive flange assembly with some degree of flexibility so that it fits the patient's body well around the stoma. When the flange is disk-shaped, its external diameter is from about 20 to 40 mm, which is greater than the diameter of the opening in conventional collecting bags, and even advantageously from 30 to 40 mm.

Since such an intubation system is removable and very easy to handle, it can be introduced and withdrawn easily by the patient himself in the case of discomfort or to replace it periodically. Furthermore, its shape prevents urine from coming into contact with the patient's skin and with the part of the plate adhering to the skin, since the urine collecting bag will be attached directly or by way of a conducting pipe to the outer face of the plate.

The invention will now be described in greater detail with the aid of some embodiments, which are chosen by way of illustration and are in no way limiting, with particular reference to the attached figures:

FIG. 1 is a schematic perspective view of a device according to the invention with an internal tube for a single ureterostomy.

The single tube device according to the invention consists of a hollow tube 2 into which the urine passes, and an integral flange 1 which demarcates on the tube a longer part, which is advantageously conical and narrower finer at the free end and which will be introduced into the ureter by the patient himself, optionally under medical supervision; the adhesive face 3 of the flange is located on the same side as this longer part 4 of the tube. Towards the end of the shorter part 2 of the tube, which is located outside the patient's body, there are advantageously perforations 5 which, in a preferred embodiment, are diametrically opposed. Before use, the adhesive part 3 is covered with a protective sheet.

The twin-tube device for double ureterostomy comprises two tubes 4 of cross-sectional diameter 2 to 4 mm, which are parallel and 1 to 10 mm apart to suit the relative position of the two stomata formed on the patient's body; these two tubes unite at the flange to form a single tube 2 of substantially double the internal diameter, and shorter, through which the urine will pass directly into the collecting bag or into a pipe connected to a collecting bag located outside the peristomal zone. In another embodiment of the device of the invention, the two tubes simply come into contact according to a generatrix of the hollow tube.

In some devices according to the invention, the perforations 5 can be absent. They are, however, preferable, and their number can be between one and a dozen, with a diameter smaller than 1/10 mm. They must be adequate to provide for discharge of the urine into the collecting bag in the case where the face of the latter comes to adhere to the end of the tube of the device, without however making the end of the said tube excessively brittle.

To use the device corresponding to one of the embodiments of the invention, after removing the protective sheet from the adhesive face of the flange, the patient introduces the longer tube 4 into the distal extremity of his ureter, or the tubes into the extremities of the ureters, until the face of the flange 3 is applied against the skin, where it adheres simply by applying pressure. He then places a collecting bag, of the type commercially available, in such a way that the part 2 of the tube passes into the bag through the opening provided in it for placing in front of the stoma. The bag is attached simply by sticking, as usual, onto the peristomal zone, which causes it to stick to the face 1 of the flange of the device and not directly to the skin, avoiding any irritation of the skin when the bag is withdrawn, since the device remains in place. The urine flows out continuously from the stoma through the tube 4 and then falls into the collecting bag at some distance from the skin, through the end of the tube 1, or through the perforations 5; this prevents the urine from coming into contact with the adhesive zones and the skin.

EXAMPLE 1

The device shown in FIG. 1 was made of polyvinyl chloride (PVC) of low hardness by injection molding.

The disk was 30 mm in diameter, 0.5 mm thick at the center and 0.1 mm at the periphery; the part 2 of the tube, which passed into the collecting bag, was 10 mm long and had an external diameter of 3.5 mm, and the tube 4, which passed into the stoma, was 50 mm long and of the same diameter. The internal diameter of this pipe was 2.8 mm, and two perforations 2 mm in diameter were made 3 mm from the end of the tube diametrically opposite each other.

The face 3 of the disk was coated with a conventional adhesive synthetic gum based on polymers and hydrocolloids, compatible with the skin and the mucosa. A siliconed paper disc covered the gum until the time of use.

EXAMPLE 2

Figure 2:
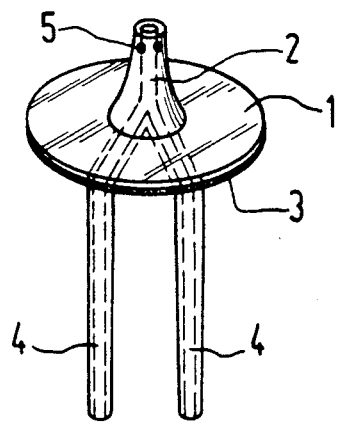
Figure 3:
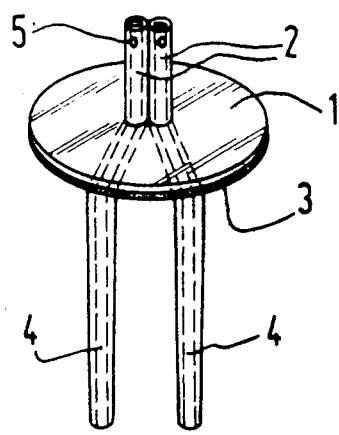

The device shown in FIG. 2 was made by injection molding from PVC of low hardness. The disk 1 was 0.5 mm thick at the center and 0.1 mm at the periphery, its diameter being 40 mm. The section 2, 10 mm long, had an external diameter of 6 mm at its end and 10 mm by the disk, while the internal diameter of the urine discharge tube was 4 mm; two diametrically opposed perforations were made, which were 3 mm in diameter and located 3 mm from the end.

The two identical tubes 4 were 50 mm long, 4 mm in external diameter and 2.8 mm in internal diameter. They were located 2 mm from each other.

The adhesive synthetic gum compatible with the mucosa was applied by cold coating. It was based on polymers and hydrocolloids.

EXAMPLE 3

The device was made from polyvinyl chloride of low hardness by injection molding. The flange 1 was in the shape of a rectangle of side dimensions 80 mm and 100 mm, with a thickness of 0.5 mm.

The section 2, 10 mm long and 5 mm average diameter, possessed a succession of 2 ribs and 2 grooves 1 mm deep at its circumference; the section 4 was 50 mm long and 4 mm in external diameter.

An adhesive gum was applied to the entire face 3 in a thickness of 1 mm.

With this device, the urine is collected in a bag attached to the user's leg. The link between the bag and the device is carried out by means of a flexible polyvinyl chloride pipe 5 mm in internal diameter which, when used, is introduced onto the section 2 of the tube of the device.

What is claimed is:

1. A removable device for discharging urine from ureterostomas, which comprises:
    (a) a hollow tube having an external diameter which enables part of it to be introduced into the body, the part comprising two branches, each of which is designed to be introduced into a stoma, and
    (b) a flange around and integral with the hollow tube and located so that said part is between 30 mm and 60 mm long, the flange being provided, on a face which will be towards a patient's body, with a material capable of adhering to skin.

2. A device as claimed in one of claim 1, in which the flange is of such a size that it can completely cover an inflow opening of a urine collecting bag and, when the bag is so provided, can cover an adhesive zone of the bag.

3. A device as claimed in claim 1, in which the flange is of such a size that it can completely cover an inflow opening of a urine collecting bag and, when the bag is so provided, can cover an adhesive zone of the bag.

4. A device as claimed in claim 1, in which the part of the tube which passes into the stoma has a smaller diameter towards its end.

5. A device as claimed in claim 2, in which the part of the tube which passes into the stoma has a smaller diameter towards its end.

6. A device as claimed in claim 3, in which the part of the tube which passes into the stoma has a smaller diameter towards its end.

7. A device as claimed in claim 1, in which the hollow tube is provided with lateral perforations near the end of the tube which remains outside the body.

8. A device as claimed in claim 2, in which the hollow tube is provided with lateral perforations near the end of the tube which remains outside the body.

9. A device as claimed in claim 3, in which the hollow tube is provided with lateral perforations near the end of of the tube which remains outside the body.

10. A device as claimed in claim 4, in which the hollow tube is provided with lateral perforations near the end of the tube which remains outside the body.

11. A device as claimed in claim 5, in which the hollow tube is provided with lateral perforations near the end of the tube which remains outside the body.

12. A device as claimed in claim 6, in which the hollow tube is provided with lateral perforations near the end of the tube which remains outside the body.

* * * * *